(12) United States Patent
Mulholland

(10) Patent No.: US 10,799,285 B2
(45) Date of Patent: Oct. 13, 2020

(54) SKIN REJUVENATION RESURFACING DEVICE AND METHOD OF USE

(75) Inventor: R. Stephen Mulholland, Toronto (CA)

(73) Assignee: INMODE LTD., Yokneam (IL)

( * ) Notice: Subject to any disclaimer, the term of this patent is extended or adjusted under 35 U.S.C. 154(b) by 1751 days.

(21) Appl. No.: 12/573,923

(22) Filed: Oct. 6, 2009

(65) Prior Publication Data
US 2010/0023003 A1    Jan. 28, 2010

Related U.S. Application Data (63) Continuation-in-part of application No. 11/315,841, filed on Dec. 22, 2005, now Pat. No. 7,618,429, and a continuation-in-part of application No. 12/555,914, filed on Sep. 9, 2009, now abandoned.

(51) Int. Cl.
| A61B 18/14 | (2006.01) |
| A61B 17/20 | (2006.01) |
| A61B 18/00 | (2006.01) |
| A61B 17/00 | (2006.01) |
| A61B 18/20 | (2006.01) |

(52) U.S. Cl.
CPC ........ *A61B 18/1477* (2013.01); *A61B 17/205* (2013.01); *A61B 18/203* (2013.01); *A61B 2017/00747* (2013.01); *A61B 2017/00765* (2013.01); *A61B 2017/00792* (2013.01); *A61B 2018/00452* (2013.01)

(58) Field of Classification Search
CPC ........... A61B 2018/00452; A61B 2017/00747; A61B 2017/00765; A61B 2017/00792; A61B 2018/0047; A61B 18/1477

USPC .................... 606/27–32, 41–44; 607/96–102
See application file for complete search history.

(56) References Cited

U.S. PATENT DOCUMENTS

| | | | |
|---|---|---|---|
| 3,193,908 A | 7/1965 | White | |
| 3,918,449 A | 11/1975 | Pistor | |
| 4,565,189 A | 1/1986 | Mabuchi | |
| 5,471,102 A | 11/1995 | Becker et al. | |
| 5,549,640 A | 8/1996 | Fontenot | |
| 5,593,381 A | 1/1997 | Tannenbaum et al. | |
| 5,941,251 A * | 8/1999 | Panescu et al. | 128/899 |
| 5,968,063 A | 10/1999 | Chu et al. | |
| 6,024,706 A | 2/2000 | Hsiao | |
| 6,090,790 A | 7/2000 | Eriksson | |
| 6,251,100 B1 | 8/2001 | Flock et al. | |
| 6,628,990 B1 * | 9/2003 | Habib et al. | 607/101 |
| 6,960,214 B2 | 11/2005 | Burkinshaw | |
| 7,066,908 B2 | 6/2006 | Kuracina et al. | |
| 7,416,541 B2 | 8/2008 | Yuzhakov et al. | |
| 8,699,908 B2 | 4/2014 | Kikuchi et al. | |
| 2003/0212397 A1 * | 11/2003 | Avrahami et al. | 606/41 |
| 2004/0019371 A1 | 1/2004 | Jaafar et al. | |
| 2004/0116953 A1 | 6/2004 | Dixon | |

(Continued)

OTHER PUBLICATIONS

Anastascalcis Dr. K. "Percutanous Delivery! The Dermaroller Series." May 2005.

*Primary Examiner* — Linda C Dvorak
*Assistant Examiner* — Samantha M Good
(74) *Attorney, Agent, or Firm* — Allen Dyer Doppelt & Gilchrist, PA (57) ABSTRACT

A skin rejuvenation resurfacing apparatus comprising an oscillating, reciprocating high speed, needle-based device and its related procedure for inducing mechanical trauma to an area of the skin to be treated.

12 Claims, 7 Drawing Sheets

(56) References Cited

U.S. PATENT DOCUMENTS

| | | |
|---|---|---|
| 2005/0203575 A1 | 9/2005 | Carson et al. |
| 2005/0222565 A1* | 10/2005 | Manstein ........................ 606/41 |
| 2006/0047281 A1 | 3/2006 | Kreindel |
| 2007/0073217 A1 | 3/2007 | James |
| 2007/0129714 A1 | 6/2007 | Elkins et al. |
| 2008/0183167 A1 | 7/2008 | Britva et al. |
| 2008/0195036 A1* | 8/2008 | Merchant ................ A61N 7/00 604/24 |
| 2009/0043247 A1 | 2/2009 | Kreindel |
| 2009/0171424 A1 | 7/2009 | Britva et al. |

\* cited by examiner

SKIN REJUVENATION RESURFACING DEVICE AND METHOD OF USE

RELATED APPLICATION

This application is a continuation-in-part of U.S. patent application Ser. No. 12/555,914 filed Sep. 9, 2009, now abandoned, which is a continuation of U.S. patent application Ser. No. 11/315,841 filed Dec. 22, 2005, now U.S. Pat. No. 7,618,429.

FIELD OF THE INVENTION

The invention relates to a device in the field of aesthetic and reconstructive medicine and cosmetic surgery to enhance the appearance of skin wrinkles, skin texture, photodamage pigmentation and scars.

BACKGROUND OF THE INVENTION

The device and the procedure with which the device is used and referred to herein using punctile resurfacing was developed as a safe and effective skin rejuvenation system for the improvement of moderate wrinkles, scars, pores, pigmentation and skin texture.

In the aesthetic industry there are many procedures using devices that improve the appearance of the skin. These devices can be divided into laser, broad band light, mechanical and radiofrequency systems.

Lasers use specific wavelengths of light that penetrate the skin, bind to specific chromophores and, through a process called selective photothermolysis remove various colors and pigments from the skin. Other lasers with longer wavelengths of light enter the skin, cause nonspecific heating and improve the texture and fine wrinkling of the skin. Intense pulse light systems release many wavelengths of light at once and also improve the color and texture of the skin through selective photothermolysis. RadioFrequency technologies, use electrical current to heat the dermis (undercarpet of the skin) and stimulate some production of collagen and elastin, fibers that firm and tighten the skin. More ablative technology, $CO_2$ and Erbium laser resurfacing, chemical peels, plasma resurfacing and mechanical dermabrasion remove the outer layers of the skin, in a relatively precise fashion and through the natural healing process, new collagen and elastin is produced in the skin, improving wrinkles and texture.

Pin point, segmental or fractional injuries to the skin and dermis can be delivered by laser systems such as Fraxel™, which sends small beams of erbium glass laser wavelengths into the dermis or the Medical Roll CIT™, which is a hand held roller with widely spaced needles. The advantage of these segmental, fractional injury and puncturing procedures, is the dermis is stimulated with either a heat or mechanical trauma and the inflammatory response results in dermal remodeling and tissue healing from the surrounding "undamaged dermis and epidermis resulting in the rapid production of new collagen, elastin and ground substance with a quicker and less symptomatic recovery and ultimately, skin enhancement and rejuvenation.

U.S. publication 2006/0047281 describes a system having a plurality of pins and electrical current delivering through these pins in the skin causing coagulation of skin around the pins The development of the device described herein and the punctile remodeling procedure was designed to deploy, through the proven efficacy of the fractional approach to dermal injury, remodeling and rejuvenation with a precision, high speed, mechanical needle puncture system and procedure that would safely and effectively improve the texture and appearance of skin. The system can comprise thermal effectors to coagulate the tissue around the created wound to reduce bleeding and improve skin rejuvenation effect.

Industry and Device Comparisons

Monochromatic Lasers:

These devices use specific wavelengths of light that penetrate the skin, bind to specific chromophores and, through a process called selective photothermolysis, remove various colors and pigments from the skin. The lasers are large, expensive pieces of capital equipment, only attack specific problems or colors in the skin, are prone to laser burns, scars, can cause hyper and/or hypopigmentation and may result in user and patient ocular injuries.

Intense Broad Band Light Systems:

These systems emit multiple wavelengths of light, and through selective photothermolysis, also improve skin discoloration and, through skin heating, non-specific skin texture improvement. The systems are also large and expensive, the skin textures and wrinkle improvements are minimal and there is also the risk of skin burns, hypo or hyperpigmentation and scars.

RadioFrequency Devices:

RadioFrequency technologies, use electrical current to heat the dermis (under carpet of the skin) and stimulate some production of collagen and elastin fibers that firm and tighten the skin. The devices are relatively expensive, have only modest skin texture or wrinkle improvements, being more designed for modest skin tightening. There is also a risk of localized fat necrosis, with permanent dimpling, damage to sensory nerves and scarring.

Plasma Technology:

Plasma technologies use saline and electrical current to induce a thin burn on the outer surface of the skin, inducing a dermal injury which heals with increase collagen, elastin and dermal ground substance. Although these devices do produce a good improvement in wrinkles, skin tightening and texture, they are expensive pieces of capital equipment and also run the risk of scarring, hyper or hypopigmentation. The recovery from the procedure is characterized by oozing and discharge and patients are not ready for make up for 2 weeks.

Laser Resurfacing and Chemical Peel:

Carbon Dioxide or Erbium lasers are used to burn off the outer layer of skin inducing a thermal injury in the dermis which heals by remodeling and increased collagen and elastin production. Resurfacing lasers also produce good wrinkle and texture improvements with skin tightening, but are expensive can potentially cause scars and profound hypopigmentation and ocular injury and blindness to the user and the patient. The recovery from the procedure is characterized by oozing and discharge and patients are not ready for make up for 2 weeks. There are also newer fractional carbon dioxide and erbium ablative lasers that deliver a fractional "ablative" segmental injury to the dermis.

Fraxel Laser:

Fraxel is a fractional, non-ablative dermal injury system that functions by emitting beams of erbium glass laser energy that creates multiple small holes in the dermis, alongside uninjured skin. The fractional dermal injury results in the remodeling without the significant recovery. The fraxel laser is expensive, and has modest results at best.

Medical Roll CIT:

This is also a fractional dermal injury system. It is a hand held roller with needles mounted on the roller. It is passed repeatedly by hand across the skin creating a dermal injury but leaving a large portion of the epidermis intake. There is some bruising and swelling, but very little pain, weeping or oozing. The mechanical injury to the dermis results in some structural collagen and elastic, smoothening out fine wrinkles. The needles are very long and widely spaced and the patients experience a significant amount of discomfort due to the length of the needle. The hand held nature of the device, make predictable spacing of the segmental injury imprecise.

What is needed is a procedure using a Punctile Resurfacing device. The inventor herein has developed a more efficient, fast, predictable and less painful device and procedure than the above described Medical Roll CIT device and its procedure. The present inventive using the inventor's developed PXL™ punctile resurfacing device provides for a resulting dermal remodeling that improves fine to moderate wrinkles, pigmentation and obtains skin texture improvement. Because there is no laser or thermal component to the injury, there is very little risk of hypo-pigmentation or scarring.

SUMMARY OF THE INVENTION

The present invention is a procedure and apparatus using a reciprocating hand piece that contains the equipment that causes the reciprocating and oscillating action of the device. The reciprocating hand piece provides the rapid oscillating, reciprocating back and forth ("in and out") motion of the needle tips. The tip of the reciprocator device has a screw on tip to which the needle tip attaches.

The working tip of the reciprocator or needle-based device is the needle tip. It is a series of a number of needles in a desired array or arrangement of said needles. The number of needles in the array can vary from 2-3 for small area treatment up to a few hundred.

The needle tip while reciprocating in and out rapidly will have some toggle and to prevent this, a sheath is inserted over the needle tip and a disposable plastic tip depth guide protector is inserted inside the sheath. The plastic tip can be pushed in or withdrawn to expose more or less of the needle tip. Thus, the plastic tip controls the depth of penetration.

The needle-based device is a skin rejuvenation device that works on the principle of fractional dermal injury, but induced through a high speed, needle based mechanical trauma. Once the headpiece is assembled, the plastic tip protector is advanced in or out of the sheath to set the length of the punctile needles that will be exposed to the skin during the treatment, providing a controllable "depth gauge" for the depth of dermal injury.
The needle array comprising one or more needles can be moved over the tissue surface using a robotic scanning mechanism or manually. The required wound depends on the treatment indication and aggressiveness of treatment, but typically in the range of 30 to 1000 holes or wounds per square centimeter.

Anesthesia:

The patient is usually anesthetized with local or topical anesthesia. The upper and lower lips, lower eyelids, frown line region and any area of acne scarring can by infiltrated with local anesthesia and treated.

Punctile Resurfacing:

The hand piece and tip is placed over the skin with direct contact of the needle tip with the skin. By activating the device, the reciprocating oscillations ("in and out" motions of the needle tip) begin and, with each reciprocation the needles penetrate into the dermis, according to the depth that was set on by the adjustment of the plastic tip protector. The hand piece is then passed over the treated area. A few passes can be applied to the same area to increase treatment effect. With each pass there is a small amount of pin-point bleeding, which stops very quickly, due to the fractional nature of the injury and the presence of bridging epidermal skin segments. Most of the trauma is dermal and ecchymosis (bruising) is induced under the skin. It is the post dermal inflammation that will determine the level of new dermal substrate formation. After each pass, the small amount of blood residual on the surface is wiped off, clotting occurs very quickly and the next pass initiated. In order to reduce bleeding, thermal energy can be applied to coagulate the blood vessels in the wound. To coagulate the blood, the needles can be preheated prior to each insertion or RF energy can be applied to the needles. Amount of thermal or RF energy delivered to the tissue is controlled by dwelling time of the reciprocating mechanism.

For example at a reciprocating rate of 100 Hz, the dwelling time is 10 ms and for 40 Hz the dwelling time is 25 ms.

In order to deliver 0.5 J at frequency of 40 Hz the power of 20 W should be applied. The required energy depends on needle diameter and length, number of needles and reciprocating frequency. The preferred range of power is from 10 W up to 500 W.

Thermal power can be delivered in form of RF energy. The preferred frequency range is from 200 kHz up to 10 MHz.

Alternatively, in order to coagulate blood vessels, the needles can be preheated prior to insertion. The needle temperature should exceed 60 degrees centigrade but not higher than 200 degrees centigrade to avoid tissue carbonization and eschar. The needles can be heated using electromagnetic energy or by contact with a pre-heated thermostat. Particularly, the electromagnetic energy can be in form of magnetic field, laser radiation, incoherent light or alternatively contact heating can be used to preheat the needle array. Electromagnetic energy can be applied in pulsed manner and synchronized with needle array reciprocation.

Reciprocation of needles can be done using a solenoid, motor with eccentric mechanism or piezoelectric element.

Reciprocation depth depends on application and can be in the range from 0.5 mm up to 500 mm Punctile Resurfacing End Point:

After about one to 6-9 criss-crossing, circular or linear passes on the skin, there will be a deep bruised discoloration to the skin and edema. Once the ecchymotic, bruised discoloration and edema has eliminated or greatly reduced the wrinkle, scar or textural abnormality and the color of the dermal bruise is dark blue, the end point of treatment has arrived. Generally an upper lip or lower lid sized zone takes 10 minutes to reach the therapeutic end point.

Post-Punctile Resurfacing Care:

As punctile resurfacing is a fractional injury, there is a microscopic but substantial area of the epidermis that is intact. The intact epidermis affects a very rapid hemostatic effect and re-epithelialization repair. As a consequence, the patients punctile resurfacing area, although bruised in appearance, exhibits minimal oozing and discomfort as the superficial epidermis is re-epithelialize within 24-48 hours. Cleansing with water and a topical emollient, such as Polysporin™ ointment is the only after care.

Punctile Resurfacing Results:

Over the 6-12 weeks post-punctile resurfacing, the bruising and edema resolves in 4-5 days and the patient may wear makeup. By 3-4 months, the mechanical trauma and inflammation that was induced by the fractional needle punctures has induced a post inflammatory reaction resulting in new dermal collagen, elastin and ground substance production. The clinical results are smoother wrinkles, improvement in depressed scars, pores, brown discoloration and enhanced skin texture.

Features of the needle-based device that are used and/or beneficial in the novel procedure are the more closely spaced needle configuration for more precise fractional dermal injury, possible pre-heating of the needles, the reciprocating mechanical handpiece for more rapid and predictable treatment of areas, the adjustable tip for more control over the depth of the dermal injury, the hand held motor, comfortable, light and AC out of the wall power source (although DC current is also contemplated), the disposable needle tip and plastic tip guide, the device headpiece and sheath can be reused, the low cost of operation, the fact that the procedure does not use a laser device to directly create the fractional injury (but a laser or RF feature may be used to heat the needle), making it safer for the operator and patient, and that there is little risk of scars or hypopigmentation as needle-based device causes a non-thermal mediated injury.

The inventive procedure is a skin rejuvenation resurfacing procedure comprising performing a punctile resurfacing procedure using an oscillating, reciprocating high speed, non-thermal or thermal, needle-based device for inducing mechanical trauma to an area of the skin to be treated.

A desired number of passes are made over the surface area of the skin to be treated in a criss-crossing, circular or random pattern until there is a deep bruised discoloration and edema to the area of the skin being treated such that a wrinkle, scar or textural abnormality being treated has been eliminated or greatly reduced.

After the procedure is completed using the needle-based device, the area of the skin treated is cleansed and a topical emollient is applied.

The resultant bruising and edema resolves in 4-5 days such that make-up may be worn on the treated area, and the mechanical trauma and inflammation that was induced by fractional needle punctures and the post inflammatory reaction results in new dermal collagen, elastin and ground substance production thereby resulting in smoother wrinkles, improvement in depressed scars and enhanced skin texture.

Prior to starting the resurfacing treatment, the patient being treated may be anesthetized with local and/or topical anesthesia to the area of the skin to be treated.

DETAILED DESCRIPTION OF THE INVENTION

Referring now to the drawings, FIGS. 1, 2A, 2B, 3, 4A, 4B, 5 and 6 disclose an example of the major system components used in the invention. Reference to these components will be made in describing the inventive procedure.

The invention is a skin rejuvenation resurfacing procedure and its associated apparatus wherein a punctile resurfacing procedure is performed on a subject patient using an oscillating, reciprocating high speed, non-thermal or thermal, needle-based device 12 for inducing mechanical and/or electrocoagulative trauma to an area of the skin to be treated. Prior to commencing the procedure, the patient being treated is anesthetized with local and/or topical anesthesia to the area of the skin to be treated.

A desired number of passes are made over the surface area of the skin to be treated in a criss-crossing, circular or random pattern until there is a deep bruised discoloration and edema to the area of the skin being treated such that a wrinkle, pigmentation, scar or textural abnormality being treated has been eliminated or greatly reduced.

The skin area to be treated is treated using the needle-based device 12 by passing in a first direction. Then an alternating pass is done in a generally criss-crossing, random or circular pattern to the first direction and the treatment is repeated in this alternating criss-crossing, random or circular pattern. The typical desired number of passes made over the area of the skin to be treated in the criss-crossing pattern is one to 20 or more passes in each direction of the criss-crossing, circular or random pattern.

After this step is completed, the area of the skin treated is cleansed and a topical emollient, such as Polysporin™ anti-bacterial ointment is applied.

The resultant bruising and edema resolves in 4-5 days such that make-up may be worn on the treated area, and the mechanical trauma and inflammation that was induced by fractional needle punctures and the post inflammatory reaction results in new collagen, elastin and ground substance production thereby resulting in smoother wrinkles, improvement in depressed scars, lessened pigmentation and enhanced skin texture.

Figure 1:
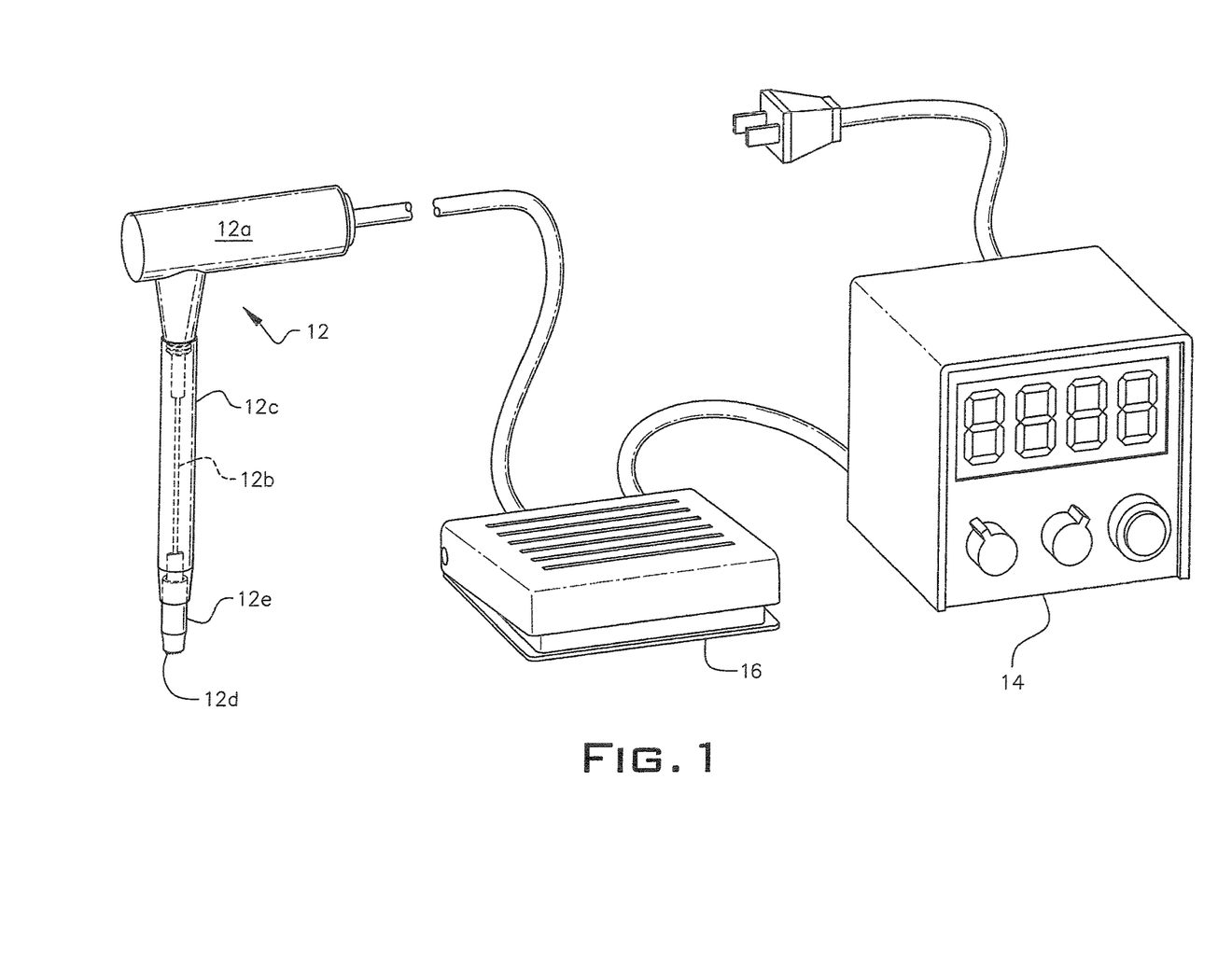
FIG. 1 is a representative schematic depiction of one example of the major system components used in the invention.

The needle-based device 12 is a hand-held device and is the power is controlled by a hands-free means. For example, a foot pedal or foot control switch 16 is typically used in the control circuit between a power controller source 14 and the hand-held needle-based device 12. The power controller source is depicted in FIG. 1 as being powered by an alternating current source but alternatively could be powered by a direct current source.

Figure 2A:
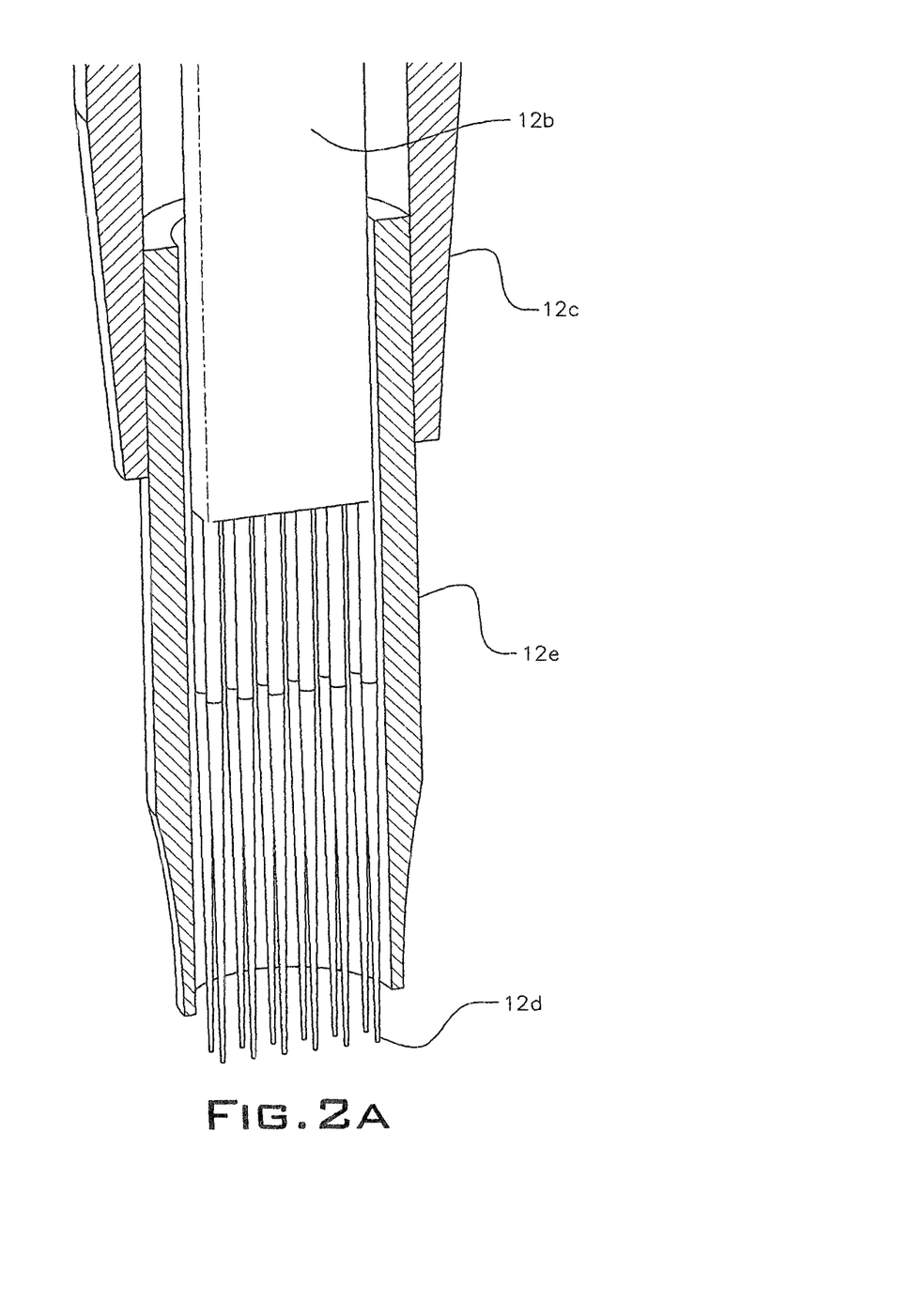
FIG. 2A is a cross-sectional view of the needle tip area.
Figure 2B:
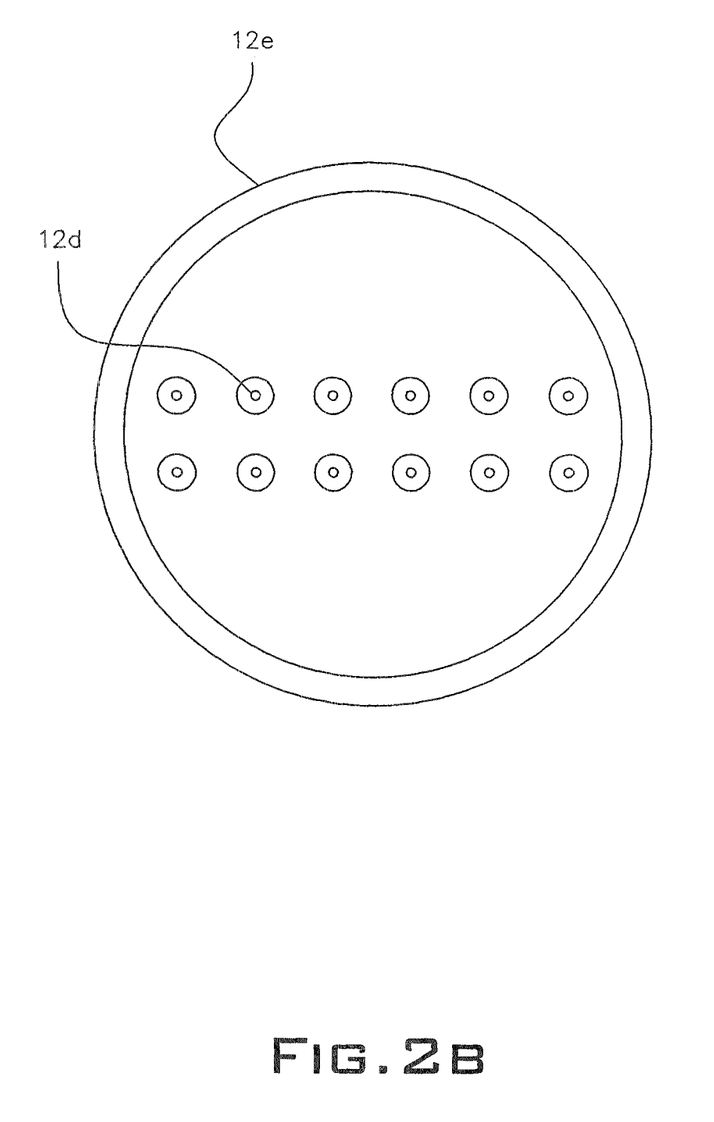
FIG. 2B is an end view of the needle tip area of FIG. 2A.
Figure 3:
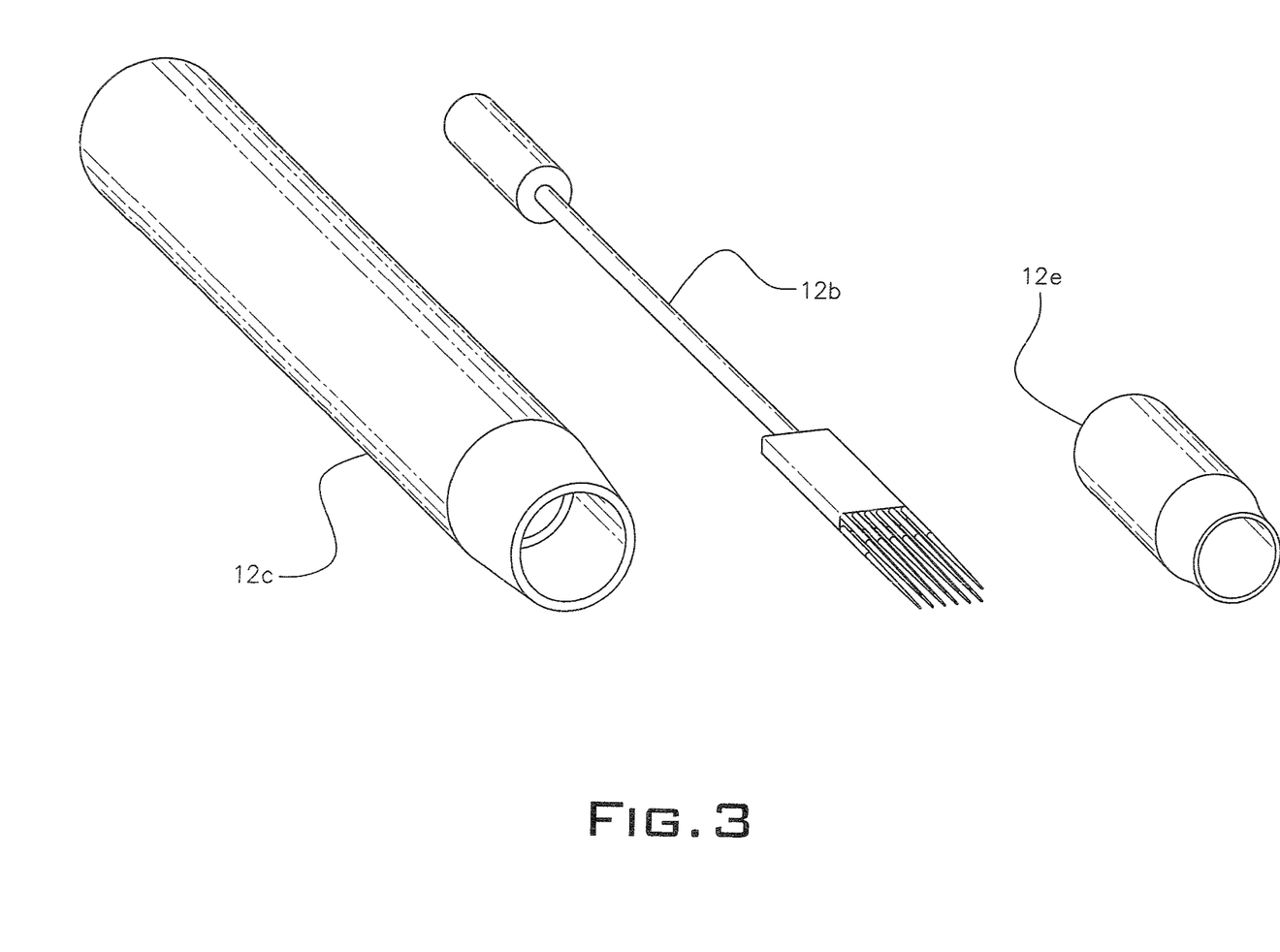
FIG. 3 is a depiction of a typical needle, needle tip sheath and needle tip plastic protector.
Figure 4A:
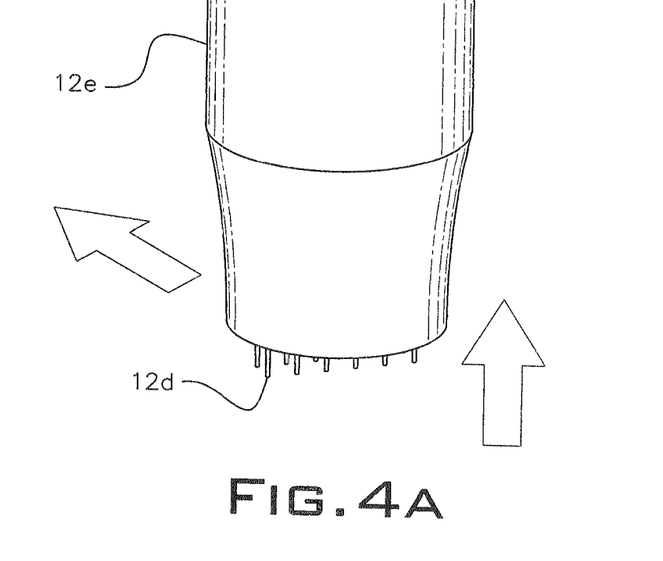
FIG. 4A is a depiction of the end of the needle tip area being directed in a path with the needles in a partially retracted position.
Figure 4B:
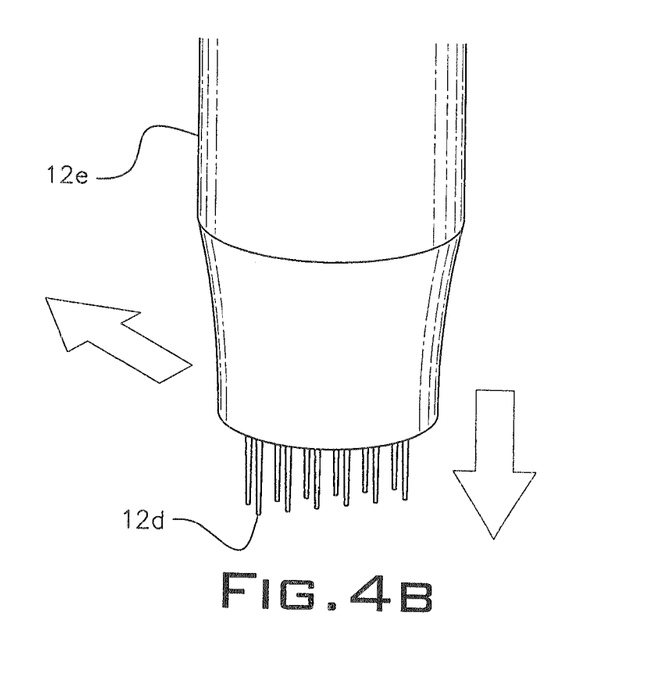
FIG. 4B is a depiction similar to FIG. 4A with the needles in an extended position.

The needle-based device includes needle depth adjustment means for obtaining a desired skin penetration depth of needle tip 12b of a plurality of needles 12d for the appropriate treatment of the area of the skin being treated. The plurality of needles 12d are preferably arranged in an array comprising between one to sixteen needles or more. For example, FIG. 2b depicts an array of 12 needles arranged in a 2×6 configuration.

The needle-based device 12 comprises a hand-held portion 12a housing means for oscillating and reciprocating an elongate needle portion 12b. This a commercially available hand piece, also referred to as head piece, which houses the motor and oscillating means (not shown) and to which the elongate needle portion 12b is connected at one end and in mechanical communication with the means for oscillating and reciprocating said needle portion 12b. Typically, the needles 12d oscillate/reciprocate at about 1 cycle per second to about 500 cycles per second.

As mentioned above, the elongate needle portion 12b has at its opposite end, a plurality of needles 12d configured in a desired array, such as 2×6.

A needle sheath 12c is provided to slide over the needle portion 12b and attach to the hand piece 12a. The attachment can be by threaded means or other methods known in the art. Sheath 12c generally covers the elongate needle portion 12b and is connected to the hand-hand portion 12a and ends with the array of the plurality of needles 12d. The needle sheath 12c further serves as means for preventing a side to side movement of the elongate needle portion 12b.

A needle tip protector 12e is attached over the plurality of needles 12d and is slidably operable over the plurality of needles 12d for serving as the needle depth adjustment means for obtaining the desired depth of needle penetration of said needle tips to the skin area being treated. Typically, the slidable protector is engaged with the end of the sheath 12c and is pushed into or pulled away from the end of the sheath 12c so that when the needle tips are extended at the maximum reciprocation distance away from hand piece 12a, the distance between the tips and the protector edge equates to the maximum penetration depth desired to accomplish the desired treatment.

Figure 5:
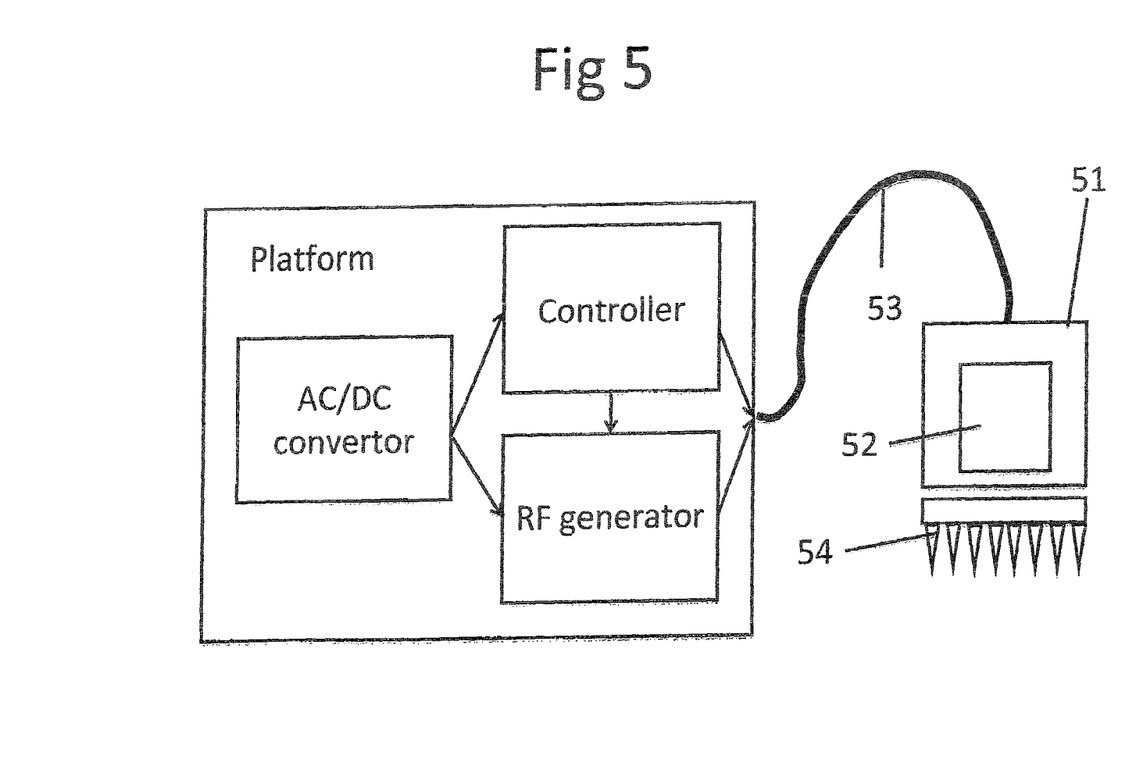
FIG. 5 is a representative block diagram of a reciprocating feature with RF energy as an optional embodiment.

An alternative embodiment shown in FIG. 5 comprises platform and hand piece 51. The platform comprises of an AC/DC convertor converting AC power from the wall plug in stabilized DC voltage, RF generator converting DC voltage from AC/DC convertor in high frequency alternating current, controller controlling RF power delivery to hand piece 51 and reciprocating speed and amplitude. Signals from controller, DC voltage and RF power are delivered to the hand piece 51 through harness 53. Hand piece comprising reciprocating mechanism 52 powered by DC voltage from AC/DC converter and controlled by controller. Needle array 54 is mechanically connected to the reciprocating mechanism 52 and electrically to the RF generator through the harness 53. RF energy is delivered to the tissue when needles get in contact with tissue and RF circuit is closed. When needle array 54 is moved back by reciprocating mechanism 52 the RF circuit is opened and RF energy delivery is terminated. RF power and reciprocation speed are adjusted to create coagulation of tissue around the needle. The heated needles may penetrate the skin and subcutaneous tissues to about from 0.5 mm to about 500 mm.

Figure 6:
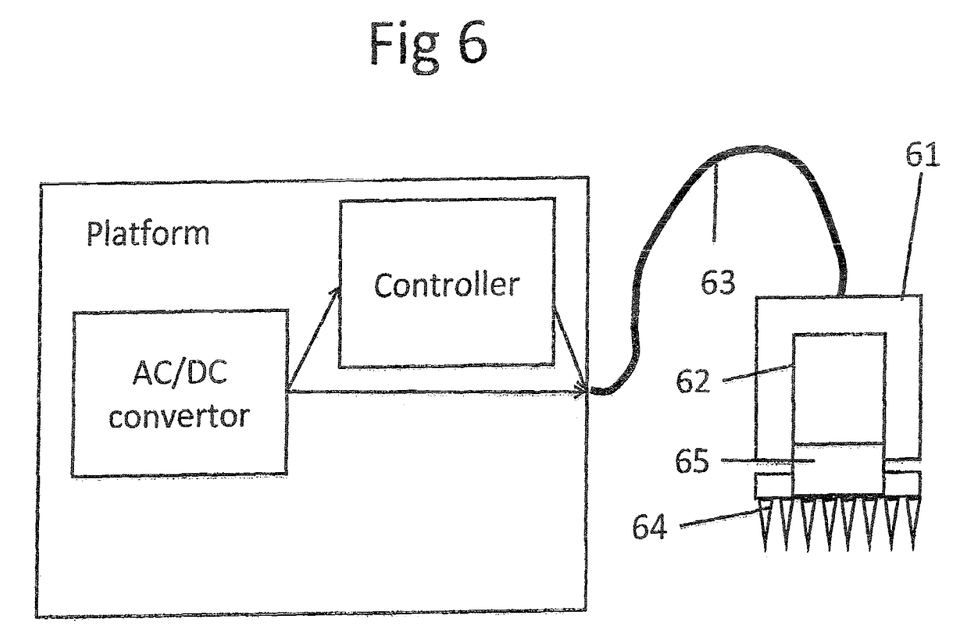
FIG. 6 is a representative block diagram of a reciprocating feature with pre-heating of needles as an optional embodiment.

Alternative embodiment shown in FIG. 6 comprises a platform and hand piece 61. The platform comprises an AC/DC convertor converting AC power from the wall plug in stabilized DC voltage, and controller controlling reciprocating speed and amplitude. Signals from the controller and DC voltage are delivered to the hand piece 61 through harness 63. Hand piece comprising a reciprocating mechanism 62 powered by a DC voltage from an AC/DC converter and controlled by a controller. Needle array 64 is mechanically connected to the reciprocating mechanism 62 and to the heating unit 65 through the harness 63. The heating unit 65 can heat the needles using electromagnetic energy or acting as a preheated thermostat. The electromagnetic energy can be in the form of a magnetic field, laser radiation, incoherent light or, alternatively contact heating. Heat from preheated needle array 64 is delivered to the tissue when needles get in contact with tissue. When needle array 64 is moved back by reciprocating mechanism 62 the needle array 64 gets in contact with heating unit 65 and heated up to the temperature predetermined by the controller.

Heating temperature and reciprocation speed are adjusted to create coagulation of tissue around the needle. The needles in the needle array may be preheated using contact with a hot element and may be preheated into the skin to the depth of from about 0.5 mm to about 500 mm.

It should be understood that the preceding is merely a detailed description of one or more embodiments of this invention and that numerous changes to the disclosed embodiments can be made in accordance with the disclosure herein without departing from the spirit and scope of the invention. The preceding description, therefore, is not meant to limit the scope of the invention. Rather, the scope of the invention is to be determined only by the appended claims and their equivalents.

What is claimed is:

1. An apparatus for use in a skin resurfacing and collagen remodeling procedure through creating of a mechanical trauma transdermally, the apparatus comprising:
    a needle array comprising a plurality of needles;
    a needle tip protector attached over the plurality of needles;
    a reciprocating mechanism connected to the needle array and providing cyclic in and out movement of the plurality of needles between a completely retracted position within the needle tip protector to a completely extended position corresponding to a maximum skin penetration depth, with oscillating frequency at a predetermined cycles per second; and
    an RF source connected to the needle array such that RF energy from the RF source is deliverable transdermally through the plurality of needles during the cyclic skin penetration;
    wherein a RF power and the oscillating frequency of the plurality of needles are set to create tissue and blood coagulation around each of the plurality of needles during skin penetration.

2. The apparatus according to claim 1, wherein the maximum skin penetration depth of the plurality of needles is adjustable from about 0.5 mm to about 500 mm.

3. The apparatus according to claim 1, wherein said oscillating frequency of said plurality of needles is about from 1Hz to 500Hz.

4. The apparatus according to claim 1, wherein a diameter of each of said plurality of needles is in a range of about 50 microns to 500 microns.

5. The apparatus according to claim 1, further comprising a scanning system that automatically moves said needle array with a predetermined speed.

6. The apparatus according to claim 1, wherein the needle array comprises a needle sheath generally covering an elongate needle portion of said needle array and ending near the plurality of needles, said needle sheath further serving as means for preventing a side to side movement of the elongate needle portion; and
    wherein the needle tip protector is attached over the plurality of needles, said needle tip protector being slidably operable over the plurality of needles for setting a desired depth of needle penetration into a skin area being treated.

7. An apparatus for use in a skin resurfacing and collagen remodeling procedure through creating of a mechanical trauma transdermally, the apparatus comprising:
- a needle array comprising a plurality of needles;
- a needle tip protector attached over the plurality of needles;
- a reciprocating mechanism connected to the needle array and providing cyclic in and out movement of the plurality of needles between a completely retracted position within the needle tip protector to a completely extended position corresponding to a maximum skin penetration depth, with oscillating frequency at a predetermined cycles per second;
- a heating unit by which heat is imparted to the plurality of needles during the cyclic movement thereof and deliverable transdermally through the plurality of needles during the cyclic skin penetration; and
- a hand piece holding the reciprocating mechanism and the heating unit;
- wherein a heating temperature of the heating unit and the oscillating frequency of the plurality needles are set to create tissue and blood coagulation around each of the plurality of needles during skin penetration.

8. The apparatus according to claim 7, wherein the maximum skin penetration depth of the plurality of needles is adjustable from about 0.5 mm to about 500 mm.

9. The apparatus according to claim 7, wherein said oscillating frequency of said plurality of needles is about from 1Hz to 500Hz.

10. The apparatus according to claim 7, wherein a diameter of each of said plurality of needles is in a range of about 50 microns to 500 microns.

11. The apparatus according to claim 7, further comprising a scanning system that automatically moves said needle array with a predetermined speed.

12. The apparatus according to claim 7, wherein the needle array comprises a needle sheath generally covering an elongate needle portion of said needle array and ending near the plurality of needles, said needle sheath further serving as means for preventing a side to side movement of the elongate needle portion; and
- wherein the needle tip protector is attached over the plurality of needles, said needle tip protector being slidably operable over the plurality of needles for setting a desired depth of needle penetration into a skin area being treated.

* * * * *